(12) United States Patent
Kessler et al.

(10) Patent No.: US 8,839,678 B2
(45) Date of Patent: Sep. 23, 2014

(54) TEST APPARATUS, COMPLIANCE MECHANISM, AND RELATED METHOD

(76) Inventors: Patrick Kessler, San Francisco, CA (US); Michael A. Damianakis, San Francisco, CA (US)

( * ) Notice: Subject to any disclaimer, the term of this patent is extended or adjusted under 35 U.S.C. 154(b) by 126 days.

(21) Appl. No.: 13/525,231

(22) Filed: Jun. 15, 2012

(65) Prior Publication Data

US 2013/0333480 A1    Dec. 19, 2013

(51) Int. Cl.
 *G01N 3/00* (2006.01)
(52) U.S. Cl.
 USPC .......................................................... 73/788
(58) Field of Classification Search
 CPC ........... G01N 3/00; G01N 3/08; G01L 5/0028
 USPC .................... 73/760, 788, 796, 797
 See application file for complete search history.

(56) References Cited

U.S. PATENT DOCUMENTS

| | | | |
|---|---|---|---|
| 3,581,558 A * | 6/1971 | Porter et al. ................. | 73/811 |
| 5,005,424 A * | 4/1991 | Markowski .................... | 73/834 |
| 5,083,463 A | 1/1992 | Marshall et al. | |
| 5,176,028 A * | 1/1993 | Humphrey .................. | 73/150 A |
| 6,250,619 B1 | 6/2001 | Cook et al. | |
| 6,262,582 B1 | 7/2001 | Barringer et al. | |
| 6,766,695 B2 | 7/2004 | Hwang | |
| 7,574,912 B2 * | 8/2009 | Fling et al. ...................... | 73/305 |

\* cited by examiner

*Primary Examiner* — Max Noori
(74) *Attorney, Agent, or Firm* — Womble Carlyle Sandridge & Rice LLP

(57) ABSTRACT

A test apparatus configured to test connectors is provided. The test apparatus may include a fixture that holds a first connector and an actuator that holds a mating second connector. The actuator may axially displace the second connector in and out of engagement with the first connector. A compliance mechanism, which may be coupled to the fixture or the actuator, may provide one of the connectors with compliance in order to facilitate alignment of the connectors during engagement and disengagement thereof. The compliance mechanism may allow movement of one of the connectors perpendicularly to the actuation axis and/or angular movement about the actuation axis while preventing axial movement within the compliance mechanism. Accordingly, forces associated with engagement and disengagement of the connectors measured by a load cell may more closely resemble actual forces experienced by a user during use of the connectors.

19 Claims, 6 Drawing Sheets

TEST APPARATUS, COMPLIANCE MECHANISM, AND RELATED METHOD

TECHNICAL FIELD

The present disclosure relates generally to a test apparatus, and more particularly to a test apparatus with a compliance mechanism configured to test connectors and a related method.

BACKGROUND

Various components of apparatuses are often tested to ensure reliability thereof and for other purposes. For example, connectors for electronic devices may be tested to ensure that they continue to function as desired despite repetitive use thereof. In this regard, connectors may be tested to ensure that the various connections therein (e.g., data, audio, electrical, etc.) continue to function after extended use thereof.

Further, it may be desirable to produce a connector which requires a satisfying amount of force to engage and disengage the connector, while not requiring so much force as to make operation of the connector difficult. Additionally, it may be desirable that the connector require consistent amounts of force to engage and disengage the connector despite repeated use thereof. In this regard, a consumer may prefer a connector that feels substantially the same during engagement and disengagement, regardless of the number of uses thereof.

Accordingly, apparatuses and methods for testing connectors may be desirable.

SUMMARY

A test apparatus is provided. The test apparatus may be configured to test engagement and/or disengagement of mating pairs of objects such as connectors. The test apparatus may include a fixture and an actuator. The fixture and the actuator may respectively hold first and second connectors. The actuator may displace the second component relative to the first connector along an actuation axis to engage and disengage the connectors.

However, in order to facilitate alignment of the first connector and the second connector, and thereby facilitate engagement and disengagement thereof, the test apparatus may also include a compliance mechanism. The compliance mechanism may be coupled to one of the fixture and the actuator and a respective one of the connectors. In order to facilitate engagement and disengagement of the connectors, the compliance mechanism may allow the connector coupled thereto to move perpendicularly relative to the actuation axis. For example, the connector may translate and or rotate. Further, in order to prevent affecting any load measurements being taken by a load cell, the compliance mechanism may be rigid along the actuation axis and thus prevent movement of the connector coupled thereto relative to the actuator or fixture to which the compliance mechanism is also coupled.

In order to control movement in this manner, an example embodiment of a compliance mechanism may include a plate and a base with ball bearings therebetween. Spring units may compress the plate and base together such that the ball bearings are compressed therebetween with a force greater than a retraction force associated with disengaging the connectors, in order to prevent axial movement within the compliance mechanism. The ball bearings may allow the plate to rotate and/or shift position perpendicularly to the actuation axis such that the connector coupled to the plate by a holder is provided with compliance. The compliance mechanism may additionally allow for angular movement (e.g., tilt) of the connector to further facilitate engagement and disengagement of the connectors.

Other apparatuses, methods, features and advantages of the disclosure will be or will become apparent to one with skill in the art upon examination of the following figures and detailed description. It is intended that all such additional systems, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures and arrangements for the disclosed assemblies, methods, and systems. These drawings in no way limit any changes in form and detail that may be made to the disclosure by one skilled in the art without departing from the spirit and scope of the disclosure.

DETAILED DESCRIPTION

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details. In other instances, well known process steps have not been described in detail in order to avoid unnecessarily obscuring the present disclosure. Other applications are possible, such that the following examples should not be taken as limiting.

Connectors are employed in a large variety of devices to establish connections. To ensure that the connectors function as desired, the connectors may be subjected to testing. For example the ability to establish repeatable successful connections (e.g., mechanical, pneumatic, hydraulic, and/or electric connections) may be desirable to ensure the connectors exhibit suitable longevity. Further, connectors may be tested for other reasons, for example to measure the forces associated with engagement and disengagement thereof. Accordingly, test apparatuses may be designed and configured to test connectors for a variety of purposes.

Figure 1:
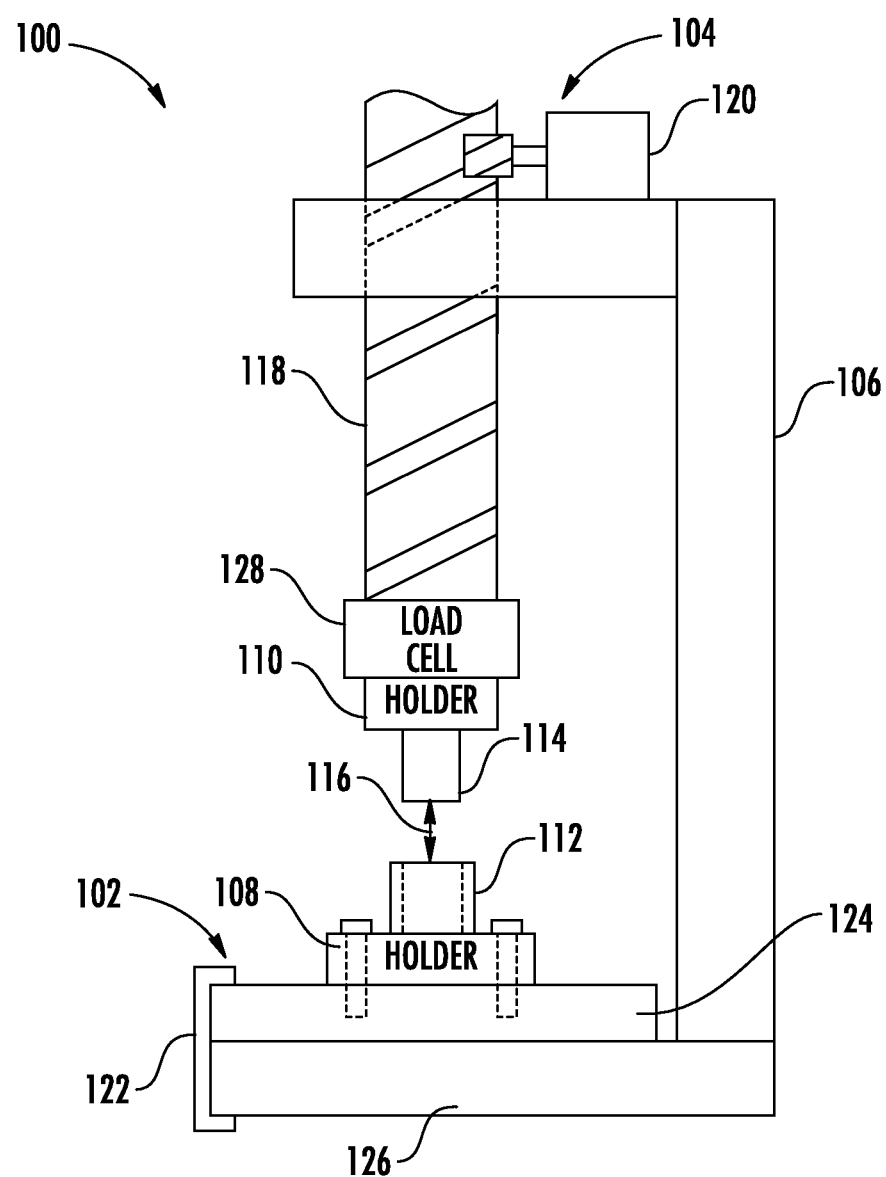
FIG. 1 illustrates a side view of a test apparatus for connectors comprising an actuator and a fixture according to an example embodiment of the present disclosure.

In this regard, FIG. 1 illustrates a first example embodiment of a test apparatus 100. As illustrated, the test apparatus 100 may comprise a fixture 102 and an actuator 104. Both the fixture 102 and the actuator 104 may be attached to a stand 106. The stand 106 may be substantially rigid to prevent unintended movement between the fixture 102 and the actuator 104.

The fixture 102 may comprise a first holder 108 and the actuator 104 may comprise a second holder 110. The first holder 108 and the second holder may be respectively configured to hold first and second connectors 112, 114. The connectors may comprise any pair of connectors configured to mate in any of a number of manners (e.g., mechanically, pneumatically, hydraulically, electronically, etc.).

The test apparatus 100 may be configured to engage and disengage the connectors 112, 114 by providing for relative movement therebetween. In the illustrated embodiment the actuator 104 is configured to displace the second connector 114 relative to the first connector 112 along an actuation axis 116. In particular, the illustrated embodiment of the actuator 104 includes a threaded shaft 118 which is vertically displaceable along the actuation axis 116 by a motor 120. However, various other displacement mechanisms such as servos, pneumatic or hydraulic pistons, solenoids, etc. may be employed to axially displace the second connector 114.

Thus, an operator may position the fixture 102 such that the first connector 112 and the second connector 114 are substantially aligned with one another, and the actuator 104 may axially displace the second connector along the actuation axis 116 in and out of engagement with the first connector. The speed at which the actuator 104 displaces the second connector 114 may vary. For example, the actuator 104 may be configured to displace the second connector 114 at relatively slow rates in some embodiments (e.g., about 1 mm per minute), whereas in other embodiments the actuator may be configured to displace the second connector in and out of engagement with the first connector 112 relatively rapidly (e.g., at a rate of about 60 hz). Further, the actuator 104 may be adjustable such that a rate at which the second connector 114 moves along the actuation axis 116 may be adjustable (e.g., within the above noted limits).

However, it may be difficult to precisely align the first connector 112 with respect to the second connector 114. In this regard, an operator of the test apparatus 100 may engage the first connector 112 with the second connector while the actuator 104 is downwardly displaced, and then hold the fixture 102 in place. For example, one or more clamps 122 may be employed to clamp a base 124 of the fixture 102 to a base portion 126 of the stand 106. However, it may be difficult to clamp the base 124 of the fixture 102 in place with the clamp 122 without slightly moving the fixture. Accordingly, the first connector 112 and the second connector 114 may not be precisely aligned during use of the test apparatus 100.

Further, axially displacing the first and second connectors 112, 114 in and out of engagement may not accurately reflect engagement and disengagement of the connectors during normal use. In this regard, when a user engages and disengages a pair of mating connectors, he or she may slightly wiggle or otherwise manipulate the connectors to facilitate engagement and/or disengagement thereof. Accordingly, tests that involve axial engagement and disengagement of the connectors may not accurately reflect wear on the connectors and/or other parameters associated with engagement and disengagement of the connectors.

Depending on the particular tests being conducted, the test apparatus 100 may further comprise a load cell 128. The load cell 128 may be coupled to one of the fixture 102 and the actuator 104 and configured to measure a load transferred between the first connector 112 and the second connector 114 along the actuation axis 116, and output a signal indicative thereof. Thus, the load cell 128 may be configured to determine the forces associated with engagement and/or disengagement of the first and second connectors 112, 114. This may be useful, for example, to determine whether the forces associated with engagement and/or disengagement fall within a desired ranged. Further, the load cell 128 may be employed to determine whether the forces associated with engagement and/or disengagement of the connectors 112, 114 changes after repeated use thereof by cyclically testing engagement and disengagement.

Figure 2:
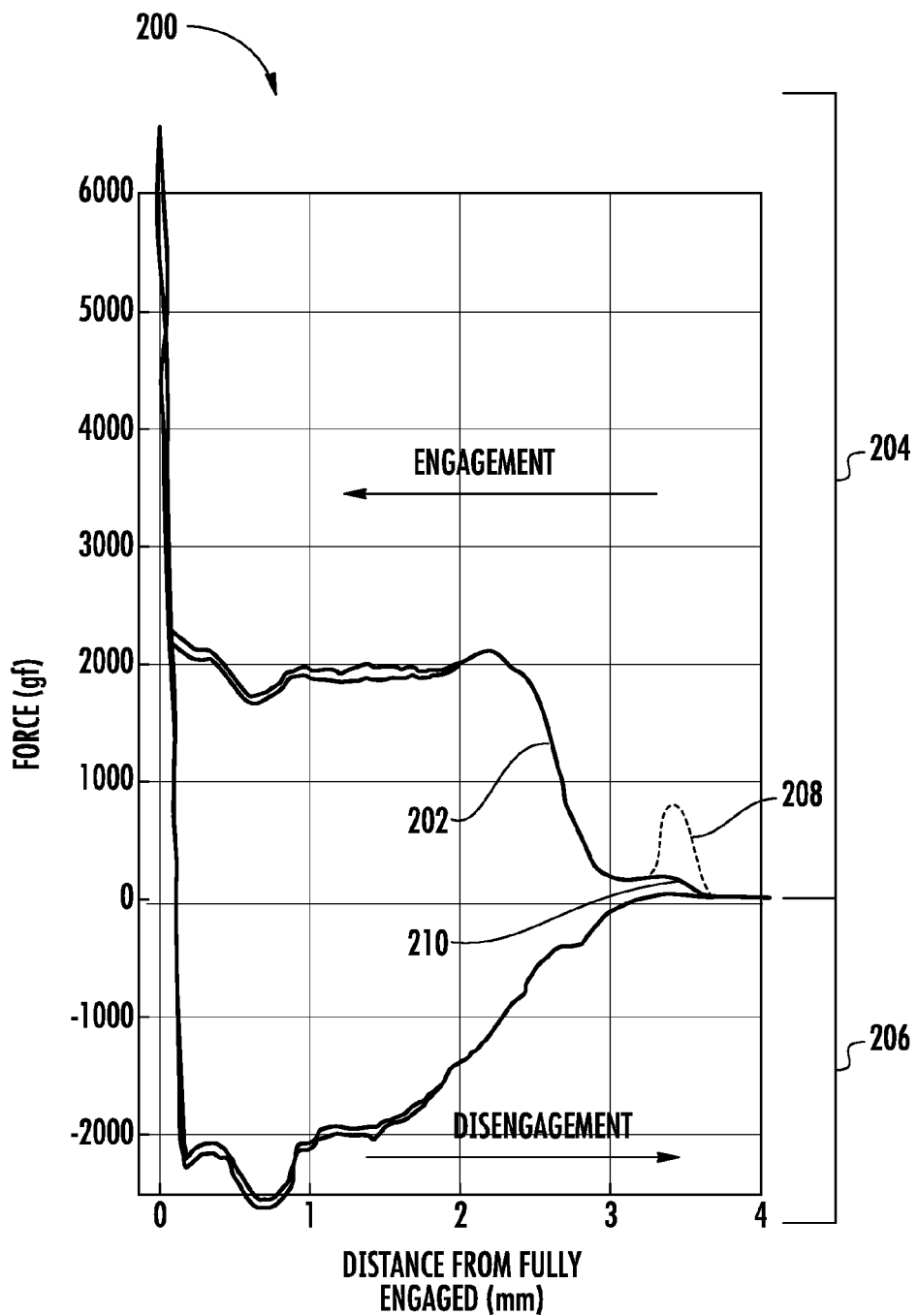
FIG. 2 illustrates a force displacement graph for engagement and disengagement of a pair of connectors according to an example embodiment of the present disclosure.

In this regard, FIG. 2 illustrates a force displacement graph 200 associated with an example pair of mating connectors. The X-axis reflects the separation distance of the two connectors from a fully engaged position, with the zero point reflecting full engagement thereof. The Y-axis reflects the force, in grams force, associated with engagement and disengagement of the connectors.

A line 202 plots the force associated with engagement and disengagement of an example pair of connectors. In particular, a first portion 204 of the data reflects engagement of the connectors, and a second portion 206 of the data reflects disengagement of the connectors. As illustrated by a dashed line, during the initial engagement of the connectors, a spike 208 in the force associated with engaging the connectors may be recorded.

However, this recorded initial spike 208 in the force may not occur during actual use of the connectors by a user. In this regard, as described above, a user may manipulate the relative positions of the connectors to facilitate alignment and engagement thereof. Thus, the initial spike 208 in the force may not be reflective of the forces associated with actual use of the connectors, which may be more accurately reflected by a corresponding portion 210 of the solid line 202. Rather, the initial spike 208 may be a byproduct of employing axial displacement of the connectors relative to one another to engage the connectors, as described above. Accordingly, it may be desirable to eliminate this initial spike 208 in force in order to more accurately reflect actual use of the connectors by a user.

Figure 3:
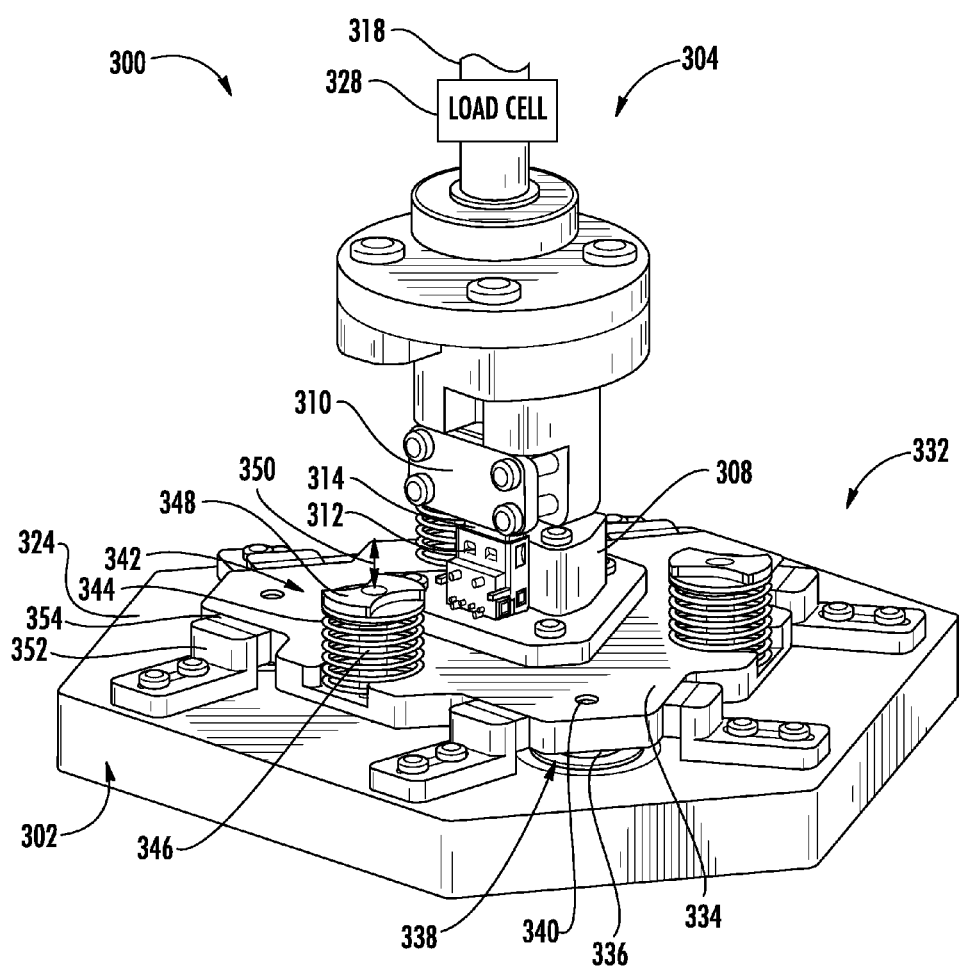
FIG. 3 illustrates a perspective view of a portion of a test apparatus for connectors comprising an actuator, a fixture, and a compliance mechanism coupled to the fixture according to an example embodiment of the present disclosure.

In this regard, FIG. 3 illustrates a second embodiment of a test apparatus 300. The test apparatus 300 may include some or all of the features described above with respect to the first embodiment of the test apparatus 100, which are similarly numbered and which will not be described in great detail for purposes of brevity. For example, the test apparatus 300 may include a fixture 302 and an actuator 304. The fixture 302 may comprise a first holder 308 and the actuator 304 may comprise a second holder 310, which are respectively configured to hold a first connector 312 and a second connector 314.

In the illustrated embodiment the first connector 312 is a female Universal Serial Bus (USB) connector, and the second connector 314 is a male USB connector. However, in other embodiments the first holder 308 may hold a male USB connector and the second holder 310 may hold a female USB connector. Further, the first holder 308 and the second holder 310 may be configured to hold various other embodiments of mating connectors, as described above.

Figure 4:
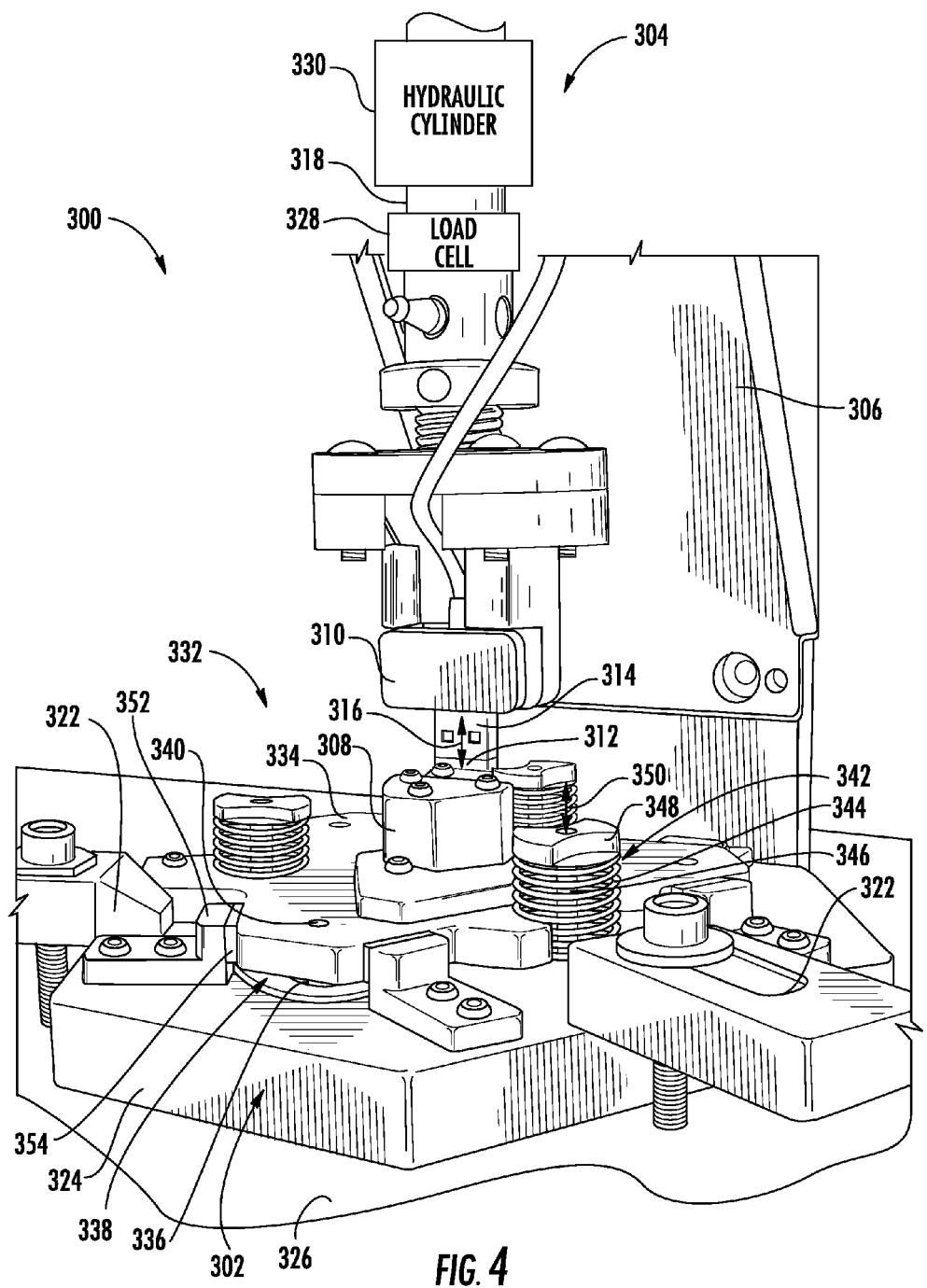
FIG. 4 illustrates the test apparatus of FIG. 3 and additional components thereof according to an example embodiment of the present disclosure.

FIG. 4 illustrates an additional perspective view of the second embodiment of the test apparatus 300 and additional components thereof. In this regard, FIG. 4 schematically illustrates the actuator 304 as comprising a hydraulic cylinder 330 that displaces a shaft 318 along the actuation axis 316. However, various other embodiments of actuators may be employed in other embodiments, as described above.

The actuator 304 may be coupled directly or indirectly to a stand 306. Further, a base 324 of the fixture 302 may be coupled to a base portion 326 of the stand 306. For example, clamps 322 may be employed to hold the fixture 302 in place after the operator aligns the first connector 312 with respect to the second connector 314. The actuator 304 may be configured to axially displace the second connector 314 relative to the first connector 312 along the actuation axis 316. A load cell 328 may output a signal indicative of the force along the actuation axis 316 associated with engaging and disengaging the connectors 312, 314. However, in order to avoid the issues described above with respect to misalignment of the connectors resulting in artificial force spikes, the test apparatus 300 may include features configured to allow for compliance of the first connector 312 relative to the second connector 314.

In this regard, as illustrated in FIGS. 3 and 4, the test apparatus 300 may further comprise a compliance mechanism 332. The compliance mechanism 332 may be configured to facilitate alignment of the first connector 312 and the second connector 314 during engagement and disengagement thereof. In the illustrated embodiment, the compliance mechanism 332 is coupled to the base 324 and the first holder 308 of the fixture 302. Accordingly, the compliance mechanism 332 may control movement between the base 324 and the first holder 308 of the fixture 302. Thereby the compliance mechanism 332 may control movement between the first connector 312 and the second connector 314.

The compliance mechanism 332 may be configured to facilitate alignment of the first connector 312 and the second connector 314 by allowing movement between the fixture 302 and the first connector 312 perpendicular to the actuation axis 316. For example, the compliance mechanism 332 may allow translation and/or rotation of the first connector 312 relative to the fixture 302. More particularly, the compliance mechanism 332 allows for translation and/or rotation of the first connector 312 relative to the base 324 of the fixture 302. In this regard, the compliance mechanism 332 in the illustrated embodiment is positioned between the base 324 and the first holder 308 of the fixture 302 such that the first holder moves with the first connector 312, but the base does not.

The compliance mechanism 332 may be configured to substantially prevent movement between the first connector 312 and the base 324 of the fixture 302 along the actuation axis 316. In this regard, it may be desirable to prevent movement between the first connector 312 and the fixture 302 along the actuation axis 316 in order to avoid affecting measurement of loads transferred between the first connector and the second connector 314 by the load cell 328. Accordingly, the compliance mechanism 332 may allow for more accurate measurements of engagement and retraction forces transferred between the first connector 312 and the second connector 314 along the actuation axis 316 by the load cell 328 associated with engagement and disengagement of the first connector 312 and the second connector 314.

The compliance mechanism may be embodied in a variety of different forms. However, in the illustrated embodiment, the compliance mechanism 332 comprises a plate 334 and the base 324 of the fixture 302 with a plurality of ball bearings 336 positioned therebetween. In this regard, all or a part of the compliance mechanism 332 may be embodied as components of the fixture 302 (or the actuator 304 in embodiments in which the compliance mechanism provides the second connector with compliance, as described below).

The ball bearings 336 may be respectively received in recessed portions 338 defined in the base 324. Further, the plate 334 may define a plurality of holes 340 that are respectively configured to align with one of the ball bearings 336. The holes 340 in the plate 334 and the recessed portions 338 defined by the base 324 may cooperate to align the plate 334 with respect to the base 324 because the ball bearings 336 may be partially received in both the holes and the recessed portions.

The compliance mechanism 332 may further comprise a plurality of spring units 342 configured to compress the ball bearings 336 between the plate 334 and the base 324. The spring units 342 may each respectively comprise a spring 344 (e.g., a coil spring) and a rod 346, which may extend through the spring. The rod 346 may be coupled to one of the plate 334 and the base 324 and configured to compress the spring 344 against the other of the plate and the base. Further, one of the base 324 and the plate 334 may be positioned between the springs 344 and the ball bearings 336. In the illustrated embodiment the plate 334 is positioned between the springs 344 and the ball bearings 336, and each rod 346 is coupled to the base and configured to compress the springs against the plate.

As illustrated, the spring units 342 may each comprise a retainer 348 coupled to one of the rods 346 and engaged with an end of a spring 344. A position of the retainer 348 along an axis 350 defined by the spring 344 may be adjustable. By way of example, the rod 346 and one of the base 324 and the retainer 348 may be threaded such that rotating the retainer compresses the spring 344 to a greater or lesser extent, depending on the direction of rotation. Accordingly, the compressive force applied by the springs 344 may be adjusted.

Note that the springs 344 may be configured to compress the ball bearings 336 with a force that is greater than a retraction force associated with disengaging the first connector 312 and the second connector 314. Accordingly, the compliance mechanism 332 may substantially prevent movement between the first connector 312 and the base 324 of the fixture 302 during disengagement of the first connector and the second connector 314. Further, since the ball bearings 336 are sandwiched between the plate 334 and the base 324, the fixture 302 rigidly prevents movement of the plate during engagement of the connectors 312, 314.

However, as noted above, the compliance mechanism 332 may allow movement between the fixture 302 and the first connector 312 perpendicular to the actuation axis 316. In this regard, the plate 334 may move in any direction perpendicular to the actuation axis, for example by translating or rotating since the plate may move (e.g., by sliding/shifting, etc.) across the tops of the ball bearings 336 with the ball bearings either remaining stationary or rotating with the movement of the plate. Accordingly, as the second connector 314 is brought into and out of contact with the first connector 312, the plate 334 may accommodate engagement therebetween by moving perpendicularly to the actuation axis 316 in one or more directions.

The compliance mechanism 332 may further comprise a plurality of centering mechanisms 352, which may surround the plate 334. The centering mechanisms 352 may be configured to bias the plate 334 to a centered position therebetween. For example, the centering mechanisms 352 may include foam pieces 354 that apply a biasing force to center the plate 334 and provide a relatively small force that resists movement of the plate perpendicularly to the actuation axis 316. Thereby, the plate 334 and the first connector 312 may remain in a centered position which may assist with initial alignment of the fixture 302 with respect to the actuator 304. Further, the centering mechanism 352 may constrain movement of the plate 334 perpendicular to the actuation axis 316 to within one or more predefined limits of travel.

As described above, in one embodiment the compliance mechanism 332 may be coupled to the fixture 302. For example, as described above, the compliance mechanism 332 may be positioned between the first holder 308 and the base 324 of the fixture 302 such that there is compliance with respect to the position of the first connector 312. Thereby, the first connector 312 and the second connector 314 may engage and disengage more easily and in a manner configured to more closely mimic usage of connectors by a consumer.

Figure 5:
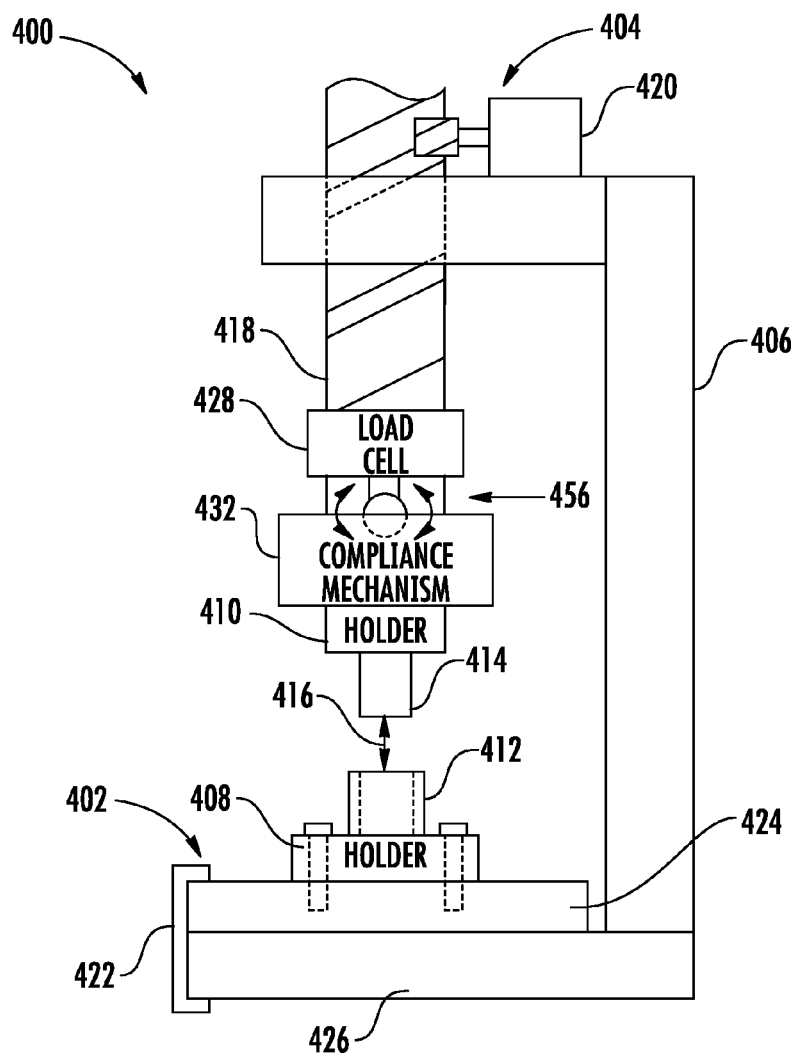
FIG. 5 illustrates a side view of a test apparatus comprising an actuator, a fixture, and a compliance mechanism coupled to the actuator according to an example embodiment of the present disclosure.

However, in an alternate embodiment, a compliance mechanism may be configured to additionally or alternatively provide compliance with respect to the position of the second connector. In this regard, FIG. 5 illustrates an embodiment of a test apparatus 400 comprising many of the components described above with respect to the test apparatus 100 of FIG. 1, which are similarly are numbered. Accordingly, these components will not be described in detail.

However, the test apparatus 400 further comprises a compliance mechanism 432, which is schematically illustrated in FIG. 5. The compliance mechanism 432 may be substantially similar to the compliance mechanism 332 described above with respect to test apparatus 300 illustrated in FIG. 4, except the compliance mechanism 432 is coupled to the actuator 404 and the second connector 414, instead of the fixture 402 and the first connector 412. Accordingly, the compliance mechanism 432 may allow the second connector 414 to move perpendicularly to the actuation axis 416 while preventing movement of the second connector along the actuation axis relative to the shaft 418.

However, the compliance mechanism 432 further differs in that it is configured to control movement by additionally allowing angular movement of the second connector 414 relative to the actuation axis 416. In this regard, the compliance mechanism 432 is illustrated as including a ball and socket joint 456 which allows the second connector 414 to tilt relative to the actuation axis 416. Accordingly, the compliance mechanism 432 provides additional compliance that may further assist in aligning the first connector 412 and the second connector 414 during engagement and disengagement thereof.

Note that embodiments of compliance mechanisms coupled to the fixture may also be configured to allow the first connector to tilt. For example, the test apparatus 300 illustrated in FIGS. 3 and 4 may further comprise a ball and socket joint between, which may be positioned between the plate 334 and the first holder 308 in one example embodiment. Note also that ball and socket joints and other mechanisms configured to provide angular compliance may include springs or other biasing mechanisms that bias the connector connected thereto to align with the actuation axis, such that initial engagement of the connectors is facilitated.

Figure 6:
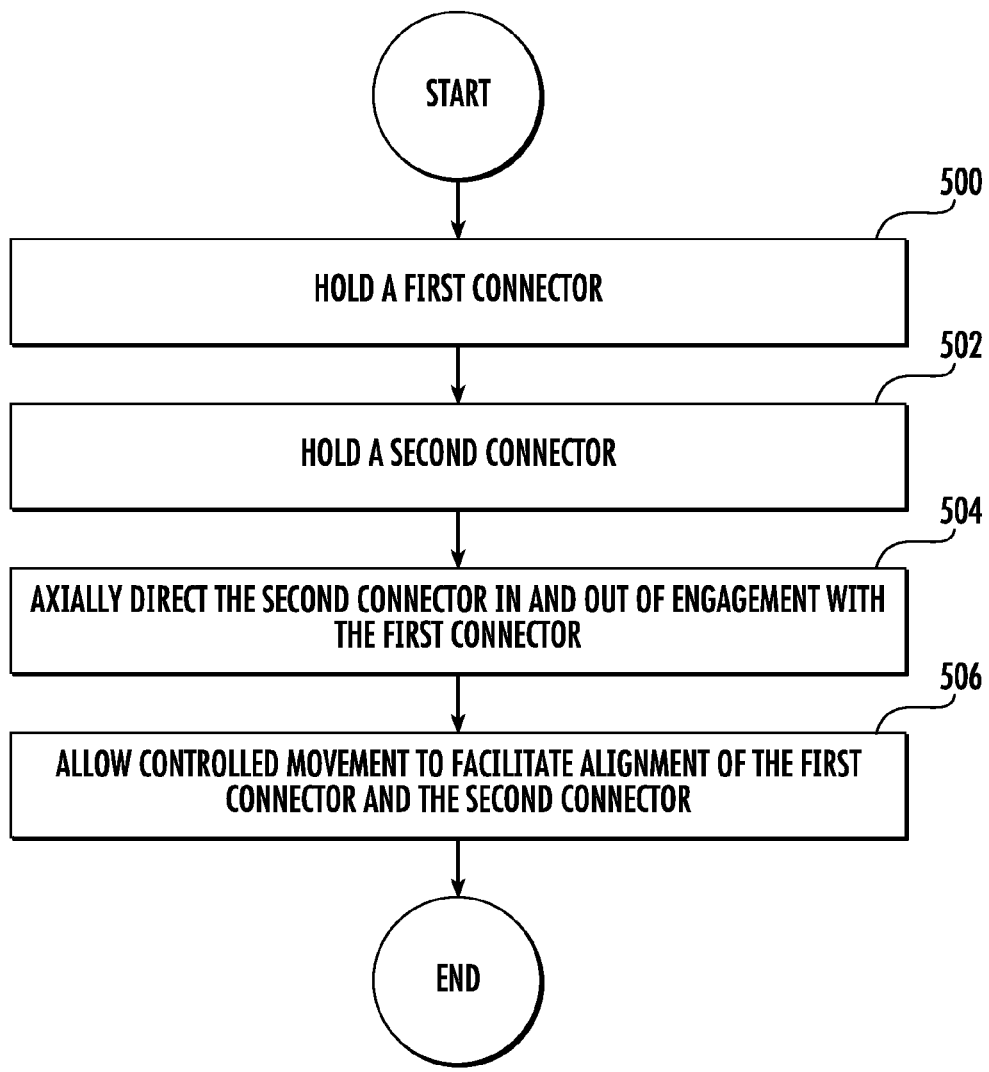
FIG. 6 illustrates a method for testing connectors according to an example embodiment of the present disclosure.

A related manufacturing method is also provided. As illustrated in FIG. 6, the method may include holding a first connector with a fixture at operation 500 and holding a second connector with an actuator at operation 502. Further the method may include directing the second connector in and out of engagement with the first connector by displacing the second connector along an actuation axis with the actuator at operation 504. Additionally, the method may include controlling movement between one of the fixture and the actuator and a respective one of the first connector and the second connector in order to facilitate alignment of the first connector and the second connector by preventing movement therebetween along the actuation axis and allowing movement therebetween perpendicular to the actuation axis at operation 506.

The method may also include measuring a load transferred between the first connector and the second connector along the actuation axis. Controlling movement at operation 506 may further comprise allowing angular movement of the respective one of the first connector and the second connector relative to the actuation axis. Controlling movement at operation 506 may also include limiting movement perpendicular to the actuation axis to within one or more predefined limits of travel. The method may additionally include biasing the respective one of the first connector and the second connector to a central position within the predefined limits of travel.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A test apparatus, comprising:
   a fixture configured to hold a first connector;
   an actuator configured to hold a second connector and displace the second connector relative to the first connector along an actuation axis to engage and disengage the first connector and the second connector; and
   a compliance mechanism configured to facilitate alignment of the first connector and the second connector, the compliance mechanism coupled to one of the fixture and the actuator and a respective one of the first connector and the second connector and configured to control movement therebetween by:
   preventing movement therebetween along the actuation axis; and
   allowing movement therebetween perpendicular to the actuation axis,
   wherein the compliance mechanism comprises a plurality of ball bearings positioned between a plate and a base.

2. The test apparatus of claim 1, further comprising a load cell coupled to one of the fixture and the actuator and configured to measure a load transferred between the first connector and the second connector along the actuation axis.

3. The test apparatus of claim 1, wherein the compliance mechanism is further configured to control movement by allowing angular movement of the respective one of the first connector and the second connector coupled thereto relative to the actuation axis.

4. The test apparatus of claim 1, wherein the compliance mechanism further comprises a plurality of springs configured to compress the ball bearings between the plate and the base.

5. The test apparatus of claim 1, wherein the springs are configured to compress the ball bearings with a force that is greater than a retraction force associated with disengaging the first connector and the second connector.

6. The test apparatus of claim 1, wherein the plate defines a plurality of holes respectively configured to align with one of the ball bearings.

7. The test apparatus of claim 6, wherein the base defines a plurality of recessed portions respectively configured to receive one of the ball bearings therein.

8. The test apparatus of claim 1, wherein the compliance mechanism further comprises a plurality of centering mechanisms configured to bias the plate to a centered position therebetween.

9. The test apparatus of claim 1, wherein the compliance mechanism comprises:
   a plate defining a plurality of holes therethrough;
   a base defining a plurality of recessed portions;

a plurality of ball bearings positioned between the plate and the base such that the plate and the base are separated in a first direction, wherein each of the ball bearings is received in one of the recessed portions in the base and aligned with one of the holes in the plate; and a plurality of spring units configured to compress the ball bearings between the plate and the base, each of the spring units comprising:
   a spring; and
   a rod coupled to one of the plate and the base and configured to compress the spring against the other of the plate and the base,
   wherein the ball bearings are configured to prevent movement of the plate in a first direction toward the base, the spring units are configured to prevent movement of the plate in an opposing second direction away from the base, and the ball bearings and the spring units are configured to allow movement of the plate relative to the base perpendicular to the first direction and the opposing second direction.

10. The compliance mechanism of claim 9, further comprising a plurality of centering mechanisms configured to bias the plate to a centered position therebetween.

11. The compliance mechanism of claim 9, wherein one of the base and the plate is positioned between the springs and the ball bearings.

12. The compliance mechanism of claim 9, wherein the spring units each comprise a retainer coupled to the rod and engaged with an end of the spring.

13. The compliance mechanism of claim 12, wherein a position of the retainer along an axis defined by the spring is adjustable.

14. The compliance mechanism of claim 9, wherein the spring comprises a coil spring and the rod is received therethrough.

15. A method for testing, comprising:
   holding a first connector with a fixture;
   holding a second connector with an actuator;
   directing the second connector in and out of engagement with the first connector by displacing the second connector along an actuation axis with the actuator; and
   controlling movement between one of the fixture and the actuator and a respective one of the first connector and the second connector in order to facilitate alignment of the first connector and the second connector by:
      preventing movement therebetween along the actuation axis; and
      allowing movement between the fixture and the first connector perpendicular to the actuation axis.

16. The method of claim 15, further comprising measuring a load transferred between the first connector and the second connector along the actuation axis.

17. The method of claim 15, wherein controlling movement further comprises allowing angular movement of the respective one of the first connector and the second connector relative to the actuation axis.

18. The method of claim 15, wherein controlling movement further comprises limiting movement perpendicular to the actuation axis to within one or more predefined limits of travel.

19. The method of claim 18, further comprising biasing the respective one of the first connector and the second connector to a central position within the predefined limits of travel.

* * * * *

UNITED STATES PATENT AND TRADEMARK OFFICE
CERTIFICATE OF CORRECTION

| | | |
|---|---|---|
| PATENT NO. | : 8,839,678 B2 | Page 1 of 1 |
| APPLICATION NO. | : 13/525231 | |
| DATED | : September 23, 2014 | |
| INVENTOR(S) | : Patrick Kessler et al. | |

It is certified that error appears in the above-identified patent and that said Letters Patent is hereby corrected as shown below:

In the Claims:

Column 8, line 50 (Claim 5, line 1): "claim 1, wherein the springs are" should read --claim 1, further comprising springs--.

Signed and Sealed this
Sixteenth Day of December, 2014

Michelle K. Lee
*Deputy Director of the United States Patent and Trademark Office*